United States Patent
Gutierrez et al.

[11] Patent Number: 5,663,427
[45] Date of Patent: Sep. 2, 1997

[54] CYSTEIC MONOSUCCINIC ACID AND ITS SALTS

[75] Inventors: Eddie Nelson Gutierrez, Midland Park; Shang-Ren Wu, Mahwah, both of N.J.

[73] Assignee: Lever Brothers Company, Division of Conopco, Inc., New York, N.Y.

[21] Appl. No.: 576,669

[22] Filed: Dec. 21, 1995

[51] Int. Cl.$^6$ .................. C07C 303/32; C07C 309/04
[52] U.S. Cl. .................................................. 562/105
[58] Field of Search ................................... 562/105

[56] References Cited

U.S. PATENT DOCUMENTS

| | | | |
|---|---|---|---|
| 3,151,084 | 9/1964 | Schlitz et al. | 510/480 |
| 3,920,564 | 11/1975 | Grecsek | 510/332 |
| 3,957,775 | 5/1976 | Lamberti | 544/110 |
| 4,397,776 | 8/1983 | Ward | 510/407 |
| 4,560,492 | 12/1985 | Curry et al. | 510/340 |
| 4,704,233 | 11/1987 | Hartman et al. | 510/337 |
| 5,183,590 | 2/1993 | Carter et al. | 252/392 |
| 5,472,642 | 12/1995 | Gutierrez et al. | 510/480 |

*Primary Examiner*—Joseph Conrad
*Attorney, Agent, or Firm*—James J. Farrell

[57] ABSTRACT

A new compound is disclosed which can be used as a builder. The compound is cysteic monosuccinic acid (CMS) and its salts as well as methods of making CMS.

4 Claims, No Drawings

CYSTEIC MONOSUCCINIC ACID AND ITS SALTS

FIELD OF THE INVENTION

The present invention relates to improved laundry detergent compositions. Specifically, it relates to a new compound, cysteic monosuccinic acid (CMS), which can be used as a builder. CMS can be used as a replacement for all or part of the builders currently used in many existing laundry products, thereby yielding detergent formulations having reduced phosphorus content. The difficulties with phosphorous containing compositions are well-documented.

Accordingly, it is highly desirable to be able to formulate detergent compositions which include reduced levels of phosphorous-containing components and are at least partially biodegradable, but which still exhibit excellent cleaning and stain removal performance.

In addition, while the use of builders in detergent compositions is desirable for enhanced stain removal, there is generally believed to be an efficacy/biodegradability trade-off with these compounds.

It is an object of the present invention to provide a compound which can be used with laundry detergent compositions requiring a relatively biodegradable chelant, that still possess excellent stain removal characteristics.

BACKGROUND OF THE INVENTION

The use of aminopolycarboxylates as builders and laundry detergent additives is generally disclosed in the art. For example, U.S. Pat. No. 4,560,491 discloses laundry detergent compositions, essentially free of phosphate detergency builders, containing an aluminosilicate or organic detergency builder and from about 0.5% to about 10% by weight of the chelant, HEDTA.

U.S. Pat. No. 4,397,776 discloses liquid laundry detergent compositions having chelating agents which include aminopolycarboxylates such as NTA, EDTA, DTPA and HEDTA.

U.S. Pat. No. 3,920,564 discloses softener/detergent formulations containing surfactants, quaternary ammonium or diamine fabric softeners, and a builder salt selected from aminopolycarboxylates and/or sodium citrate. Examples of suitable aminopolycarboxylates include NTA, EDTA and HEDTA.

U.S. Pat. No. 3,151,084 discloses detergent compositions in which solubility is said to be improved by the addition of 0.25% to 4% of a mixture of EDTA and a solubilizing agent selected from salts of N,N-di(2-hydroxyethyl) glycine, iminodiacetic acid, NTA and HEDTA. None of the patents disclose detergent compositions which contain CMS.

U.S. Pat. No. 5,183,590 discloses N-(hydroxysuccinyl) cysteic acid as a corrosion inhibitor for aqueous systems.

None of the patents disclose CMS.

SUMMARY OF THE INVENTION

The compound of this invention is CMS which can be used in laundry detergents comprising:
(a) from about 1% to about 75% by weight of a detergent surfactant selected from the group consisting of anionic surfactants, nonionic surfactants, zwitterionic surfactants, ampholytic surfactants, cationic surfactants, and mixtures thereof; and
(b) from about 5% to about 80% by weight of cysteic monosuccinic acid or alkali metal, alkaline earth, ammonium or substituted ammonium salts thereof, or mixtures thereof.

DETAILED DESCRIPTION OF THE INVENTION

Detergent Surfactant

The amount of detergent surfactant included in the detergent compositions of the present invention can vary from about 1% to about 75% by weight of the composition depending upon the particular surfactant(s) used, the type of composition to be formulated (e.g., granular, liquid, concentrate) and the effects desired. Preferably, the detergent surfactant(s) comprises from about 10% to about 60% by weight of the composition. The detergent surfactant can be nonionic, anionic, ampholytic, zwitterionic or cationic. Mixtures of these surfactants can also be used.

Cysteic Monosuccinic Acid or Salts Thereof

The compositions of the invention contain, as an essential component, from about 5% to about 80%, preferably from about 20% to about 60% of cysteic monosuccinic acid, or the alkali metal, alkaline earth metal, ammonium or substituted ammonium salts thereof, or mixtures thereof. Preferred CMS compounds for granular detergent compositions are the free acid form and the sodium salt thereof. Examples of such preferred sodium salts of CMS include NaCMS, Na$_2$CMS and Na$_4$CMS. Preferred CMS compounds for liquid detergent compositions are the free acid form and the ammonium or potassium salts thereof.

The structure of the acid form of CMS is as follows:

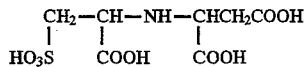

CMS (cysteic monosuccinate) is prepared by reacting disodium cysteate with either monomethyl sodium maleate or disodium bromosuccinate. The former method generates CMS and disodium maleate and fumarate as byproducts after the saponification of the methyl esters, while the latter generates sodium bromide as an impurity.

Both reaction schemes are shown as follows:

SCHEME I

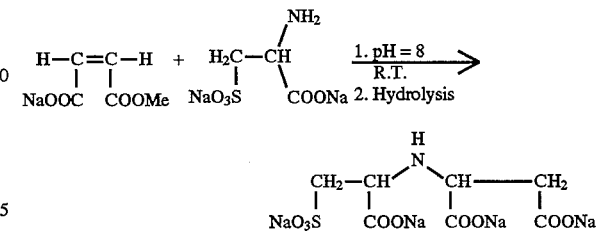

SCHEME II

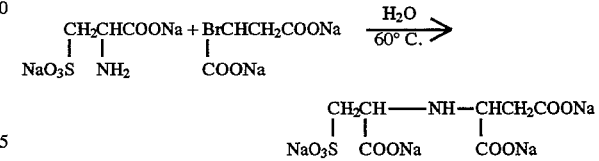

Alternatively cystine d, l or dl can be reacted with Br succinic acid salts to generate a disulfide structure which can be oxidized to CMS as follows:

SCHEME III

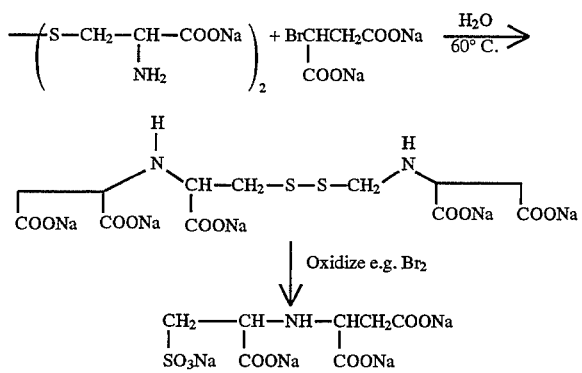

WR Grace has patented CMHS (cysteic monohydroxysuccinate) prepared from disodium cysteate and disodium epoxysuccinate. Both molecules are similar except that the WR Grace compound contains a hydroxy group adjacent to the sulfonate group.

Detergent Builders

Detergent compositions of the present invention, in addition to the CMS builder, may also contain inorganic and/or organic detergent builders to assist in mineral hardness control. These builders comprise from about 5% to about 80% by weight of the compositions. Built liquid formulations preferably comprise from about 10% to about 30% by weight of detergent builder, while built granular formulations preferably comprise from about 10% to about 50% by weight of detergent builder.

Suitable detergent builders include crystalline aluminosilicate ion exchange materials having the formula:

$$Na_z[(AlO_2)_z(SiO_2)_y] \cdot xH_2O$$

wherein z and y are at least about 6, the mole ratio of z to y is from about 1.0 to about 0.5; and x is from about 10 to about 264. Amorphous hydrated aluminosilicate materials useful herein have the empirical formula:

$$M_x(zAlO_2 \cdot ySiO_2)$$

wherein M is sodium, potassium, ammonium or substituted ammonium, z is from about 0.5 to about 2, and y is 1; this material has a magnesium ion exchange capacity of at least about 50 milligram equivalents of $CaCO_3$ hardness per gram of anhydrous aluminosilicate.

Aluminosilicate ion exchange materials useful herein are commercially available. These aluminosilicates can be crystalline or amorphous in structure and can be naturally-occurring aluminosilicates or synthetically derived a method for producing aluminosilicate ion exchange materials is disclosed in U.S. Pat. No. 3,985,669, Krummel et al, issued Oct. 12, 1976, incorporated herein by reference. Preferred synthetic crystalline aluminosilicate ion exchange materials useful herein are available under the designations Zeolite A, Zeolite P (B), and Zeolite X. In an especially preferred embodiment, the crystalline aluminosilicate ion exchange material has the formula:

$$Na_{12}[(AlO_2)_{12}(SiO_2)_{12}] \cdot xH_2O$$

wherein x is from about 20 to about 30, especially about 27.

Other detergency builders useful in the present invention include the alkali metal silicates, alkali metal carbonates, phosphates, polyphosphates, phosphonates, polyphosphonic acids, $C_{10}-C_{18}$ alkyl monocarboxylic acids, polycarboxylic acids, alkali metal ammonium or substituted ammonium salts thereof and mixtures thereof. Preferred are the alkali metal salts of the above, especially sodium.

Useful water-soluble, nonphosphorous organic builders include the various alkali metal, ammonium and substituted ammonium polyacetates, carboxylates, polycarboxylates and polyhydroxysulfonates. Examples of polyacetate and polycarboxylate builders are the sodium, potassium, lithium, ammonium and substituted ammonium salts of ethylenediamine tetraacetic acid, nitrilotriacetic acid, oxydisuccinic acid, mellitic acid, carboxymethyloxysuccinic acid, benzene polycarboxylic acids and citric acid. For purposes of defining the invention, the organic detergent builder component which may be used herein does not include CMS or its salts.

Optional Detergent Ingredients

Optional ingredients which can be included in detergent compositions of the present invention, in their conventional art-established levels for use (generally from 0% to about 20% of the detergent composition), include solvents, hydrotropes, solubilizing agents, processing aids, soil-suspending agents, corrosion inhibitors, dyes, fillers, optical brighteners, germicides, pH-adjusting agents (monoethanolamine, sodium carbonate, sodium hydroxide, etc.), enzymes, enzyme-stabilizing agents, perfumes, fabric softening components, static control agents, bleaching agents, bleach activators, bleach stabilizers and the like.

Materials that provide clay soil removal/anti-redeposition benefits can also be incorporated in the detergent compositions of the invention and are particularly useful in liquid compositions of the invention. These clay soil removal/anti-redeposition agents are usually included at from about 0.1% to about 10% by weight of the composition.

One group of preferred clay soil removal/anti-redeposition agents are the ethoxylated amines disclosed in U.S. Pat. No. 4,597,898. Soil release agents, such as those disclosed in the art to reduce oily staining of polyester fabrics, may also be used in the compositions of the present invention. U.S. Pat. No. 3,962,152 discloses copolymers of ethylene terephthalate and polyethylene oxide terephthalate as soil release agents. Cellulose ethers and various other soil release agents are also useful.

Detergent Formulations

Granular detergent compositions embodying the present invention can be formed by conventional techniques, i.e., by slurrying the individual components in water and then atomizing and spray-drying the resultant mixture, or by pan or drum agglomeration of the ingredients. Granular formulations preferably comprise from about 5% to about 40% of detergent surfactant selected from the group consisting of anionic surfactants, nonionic surfactants, and mixtures thereof.

Liquid compositions of the present invention can contain water and other solvents. Low molecular weight primary or secondary alcohols, exemplified by methanol, ethanol, propanol, and isopropanol are suitable. Monohydric alcohols are preferred for solubilizing the surfactant, but polyols containing from about 2 to about 6 carbon atoms and from about 2 to about 6 hydroxy groups can be used and can provide improved enzyme stability (if enzymes are included in the composition). Examples of polyols include propylene glycol, glycerine and 1,2-propanediol. Ethanol is a particularly preferred alcohol.

The liquid compositions preferably comprise from about 10% to about 60% of detergent surfactant, about 10% to about 30% of CMS or salts thereof as a builder.

Useful detergency builders in liquid compositions, in addition to CMS, include the alkali metal silicates, alkali metal carbonates, polyphosphonic acids, $C_{10}$–$C_{18}$ alkyl monocarboxylic acids, polycarboxylic acids, alkali metal, ammonium or substituted ammonium salts thereof, and mixtures thereof. Preferred liquid compositions contain from about 10% to about 28% of detergency builders selected from the group consisting of $C_{10}$–$C_{18}$ alkyl monocarboxylic acids, polycarboxylic acids and mixtures thereof.

Particularly, preferred liquid compositions contain from about 10% to about 18% of a $C_{10}$–$C_{18}$ monocarboxylic (fatty) acid and from about 0.2% to about 10% of a polycarboxylic acid, preferably citric acid, and provide a solution pH of from about 6 to about 10 at 1.0% concentration in water.

Preferred liquid compositions are substantially free of inorganic phosphates or phosphonates. As used in this context "substantially free" means that the liquid compositions contain less than about 0.5% by weight of an inorganic phosphate- or phosphonate-containing compound.

The detergent compositions of the invention are particularly suitable for laundry use, but are also suitable for the cleaning of hard surfaces and for dishwashing.

In a laundry method aspect of the invention, typical laundry wash water solutions comprise from about 0.1% to about 2% by weight of the detergent compositions of the invention. Fabrics to be laundered are agitated in these solutions to effect cleaning and stain removal.

All parts, percentages and ratios herein are by weight unless otherwise specified. The following examples illustrate the present invention.

EXAMPLE 1

Two g (0.02 mol) maleic anhydride are dissolved in 10 ml methanol, and the solution neutralized to pH 8 with sodium hydroxide. The solution is evaporated to dryness and the solid is dissolved in 15 cc water, followed by the addition of 3.8 g (0.02) cysteic acid monohydrate disodium salt. The mixture is stirred at pH 8 for 10–12 hr. The product is contaminated with fumarate, maleate and cysteate and trituration with methanol/water removes the former two but not the cysteate.

EXAMPLE 2

Cysteic acid, 9.3 g (0.05 mol) and bromosuccinic acid (0.01 mol) are dissolved in 100 ml water and 12 g (0.3 mol) sodium hydroxide in 50 ml water added to pH 8.5. The solution is heated to 50° C. and 3 g of NaOH added to maintain the pH below 9.2. The solution is evaporated down to 75 ml, followed by the addition of methanol to precipitate a viscous residue. The residue is triturated 5X with methanol/water to afford 12.4 g solid after drying. To obtain purified CMS, 1 g of solid is acidified and extracted with acetone, several times the residue is extracted into methanol and neutralized to pH 8 in water.

C13 NMR (50 MZ, ppm): 2 diastereoisomer $\underline{C}H_2$ COONa (s 39.4, s 40:7), $\underline{C}H_2SO_3Na$ (s 52.9, 53.2), $\underline{C}HN$ ex succinate and $\underline{C}HN$ ex cysteate (4s 58.3, 58.9, 59.2, 59.5)

EXAMPLE 3

A composition containing CMS is prepared as follows:

| | |
|---|---|
| $C_{12}$ linear alkylbenzene sulfonate | 3.5% |
| CMS | 49.7% |
| $C_{14}$–$C_{15}$ alkyl ethoxylate - 2.5 | 5.5% |
| Silicate ($SiO_2/Na_2O$ ratio = 1.6 to 1) | 4.8% |
| $Na_2SO_4$ | 25.1% |
| Polyethylene glycol (MW = 8000) | 0.4% |
| $H_2O$ and miscellaneous (color, perfume, etc.) | 11.0% |

This composition employing CMS as a builder is expected to have good cleaning properties.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A compound of the formula:

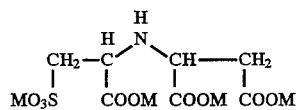

wherein M is selected from the group consisting of Na, K, Li, ammonium, substituted ammonium and mixtures thereof.

2. A compound as defined in claim 1 wherein M is sodium.

3. A process for preparing a compound of the formula:

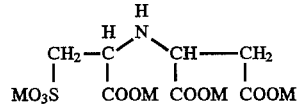

wherein M is selected from the group consisting of Na, K, Li, ammonium, substituted ammonium and mixtures thereof comprising a. reacting a monoalkyl maleate of the formula

wherein M is selected from the group consisting of Na, K, Li, ammonium and substituted ammonium and R is methyl or ethyl with b. cysteic acid salts of the formula

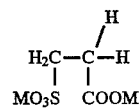

wherein M is selected from the group consisting of Na, K, Li, ammonium and substituted ammonium at a temperature of about 25° C. for about 100° C. for about 1 to 5 hours at a pH of about 8.0 to 8.6 to form said compound.

4. A process for preparing a compound of the formula:

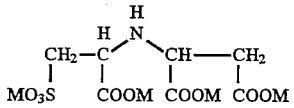

wherein M is selected from the group consisting of Na, K, Li, ammonium, substituted ammonium and mixtures thereof comprising a. reacting a monoalkylmaleate of the formula:

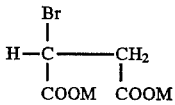

wherein M is selected from the group consisting of Na, K, Li, ammonium and substituted ammonium with b. cysteic acid salts of the formula

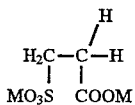

wherein M is selected from the group consisting of Na, K, Li, ammonium and substituted ammonium at a temperature of about 25° C. to about 100° C. for about 1 to 5 hours at a pH of about 8.5 to 9.2 to form said compound.

* * * * *